United States Patent
Sudo et al.

Patent Number: 5,710,148
Date of Patent: Jan. 20, 1998

[54] CORNEAL OPACIFICATION INHIBITORY COMPOSITION

[75] Inventors: Katsuichi Sudo, Osaka; Yasuko Umegaki; Yasushi Okumura, both of Hyogo, all of Japan

[73] Assignee: Senju Pharmaceuticals Co., Ltd., Osaka, Japan

[21] Appl. No.: 611,465

[22] Filed: Mar. 4, 1996

[30] Foreign Application Priority Data

Mar. 6, 1995 [JP] Japan ................... 7-045808
Jan. 10, 1996 [JP] Japan ................... 8-002444

[51] Int. Cl.$^6$ .......... A61K 31/395; A61K 31/38; A61K 31/335

[52] U.S. Cl. .......... 514/210; 514/430; 514/475; 514/912

[58] Field of Search .......... 514/210, 430, 514/475, 912

[56] References Cited

FOREIGN PATENT DOCUMENTS

| | | |
|---|---|---|
| 0354767 | 8/1989 | European Pat. Off. . |
| 0354787 | 2/1990 | European Pat. Off. . |
| 0357061 | 3/1990 | European Pat. Off. . |
| 0387650 | 3/1990 | European Pat. Off. . |
| 0415294 | 3/1991 | European Pat. Off. . |
| 0461427 | 12/1991 | European Pat. Off. . |

*Primary Examiner*—Zohreh Fay
*Attorney, Agent, or Firm*—David G. Conlin; David S. Resnick; Dike, Bronstein, Roberts & Cushman, LLP

[57] ABSTRACT

An ophthalmic preparation which comprises a fumagillol derivative represented by the general formula(I):

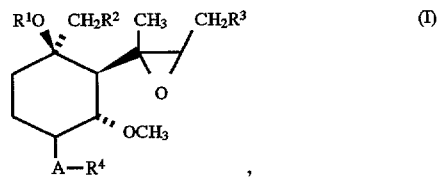

wherein $R^1$ is hydrogen; $R^2$ is a halogen, $N(O)_m R^5 R^6$, $N^+ R^5 R^6 R^7 \cdot X^-$, $S(O)_n R^5$ or $S^+ R^5 R^6 \cdot X^-$, wherein $R^5$, $R^6$ and $R^7$ represent independently a substituted or unsubstituted hydrocarbon group or a substituted or unsubstituted heterocyclic group; $X^-$ represents a counter anion; m represents 0 or 1; n represents an integer from 0 to 2; or $R^5$ and $R^6$ together with the adjacent nitrogen or sulfur atom may form a substituted or unsubstituted nitrogen- or sulfur-containing heterocyclic group which may form a condensed ring; or $R^1$ and $R^2$ are combined to represent a chemical bond; $R^3$ is a substituted or unsubstituted 2-methyl-1-propenyl group or a substituted or unsubstituted isobutyl group; A is oxygen or $NR^8$, wherein $R^8$ represents hydrogen, a substituted or unsubstituted lower alkyl group or a substituted or unsubstituted aryl group; and $R^4$ is hydrogen, a substituted or unsubstituted hydrocarbon group or a substituted or unsubstituted acyl group and a salt thereof is useful for inhibiting corneal opacification occurring after ophthalmic surgery.

4 Claims, No Drawings

CORNEAL OPACIFICATION INHIBITORY COMPOSITION

FIELD OF THE INVENTION

The present invention relates to a corneal opacification inhibitory composition comprising a fumagillol derivative or a salt thereof.

BACKGROUND OF THE INVENTION

Heretofore, steroidal antiinflammatory agents have been mainly used for inhibiting corneal opacification(i.e. haze), but there have been some concerns about their side effects such as steroidal glaucoma and aggravation of ophthalmic infectious diseases. Corneal opacification is sometimes induced after laser (e.g. excimer laser) ablation which is used as a technique to correct myopia.

The ablation of epithelium and stroma of the cornea (photorefractive keratectomy: PRK) has been widely used to correct myopia in the United States, and the research work toward its development has been carried out in Japan as well. The method is a very simple technique which changes the refraction of light in cornea by ablating the epithelium and stroma of the cornea However, when corneal epithelium is repaired, a problem that has been after surgery is corneal opacification (e.g. of the inducement of opacification which arises between epithelium and stroma of the cornea). The mechanism responsible for this opacification is not known. Topical use of interferon-α to alleviate corneal scarring after PRK with excimer laser has been proposed (JP Kohyo 501320/1995). However, its inhibiting effect of corneal opacification is not usually sufficient.

Currently there are no satisfactory inhibiting agents for corneal opacification. Thus, the development of a potent corneal opacification inhibitory agent is desired.

SUMMARY OF THE INVENTION

In view of the above mentioned problems, the present inventors after extensive search and evaluation discovered that 6-0-(N-chloroacetylcarbamoyl) fumagillol has excellent corneal opacification inhibitory effect.

Thus, the present invention is directed to:

(1) A corneal opacification inhibitory composition which comprises a fumagillol derivative represented by the general formula (I):

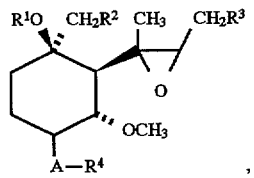

wherein $R^1$ is hydrogen; $R^2$ is a halogen, $N(O)_m R^5 R^6$, $N^+ R^5 R^6 R^7 \cdot X^-$, $S(O)_n R^5$ or $S^+ R^5 R^6 \cdot X^-$, wherein $R^5$, $R^6$ and $R^7$ represent independently a substituted or unsubstituted hydrocarbon group or a substituted or unsubstituted heterocyclic group; $X^-$ represents a counter anion; m represents 0 or 1; n represents an integer from 0 to 2; or $R^5$ and $R^6$ together with the adjacent nitrogen or sulfur atom may form a substituted or unsubstituted nitrogen- or sulfur-containing heterocyclic group which may form a condensed ring; or $R^1$ and $R^2$ are combined to represent a chemical bond; $R^3$ is a substituted or unsubstituted 2-methyl-1-propenyl group or a substituted or unsubstituted isobutyl group; A is oxygen or $NR^8$, wherein $R^8$ represents hydrogen, a substituted or unsubstituted lower alkyl group or a substituted or unsubstituted aryl group; and $R^4$ is hydrogen, a substituted or unsubstituted hydrocarbon group or a substituted or unsubstituted acyl group or a salt thereof, and an ophthalmologically acceptable carrier or excipient.

(2) A method of treating corneal opacification which comprises administering a corneal opacification inhibitory amount of a fumagillol derivative of the formula (I) or a salt thereof to a subject undergoing ophthalmic surgery, and (3) Use of a fumagillol derivative of the formula (I) or a salt thereof for treating corneal opacification occurring after ophthalmic surgery.

DETAILED DESCRIPTION OF THE INVENTION

In the present invention, any fumagillol derivative can be used as long as it exhibits an inhibitory activity against the growth of vascular cells, and examples of the fumagillol derivative include a compound represented by the formula (I) (hereinafter sometimes referred to as the compound (I)):

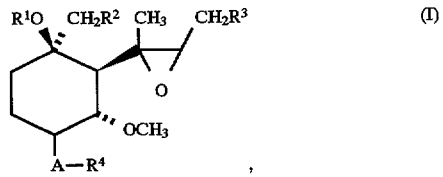

wherein $R^1$ is hydrogen; $R^2$ is a halogen, $N(O)_m R^5 R^6$, $N^+ R^5 R^6 R^7 \cdot X^-$, $S(O)_n R^5$ or $S^+ R^5 R^6 \cdot X^-$ wherein $R^5$, $R^6$ and $R^7$ represent independently a substituted or unsubsutituted hydrocarbon group or a substituted or unsubstituted heterocyclic group; $X^-$ represents a counter anion; m represents 0 or 1; n represents an integer from 0 to 2; or $R^5$ and $R^6$ together with the adjacent nitrogen or sulfur atom may form a substituted or unsubstituted nitrogen- or sulfur-containing heterocyclic group which may form a condensed ring; or $R^1$ and $R^2$ are combined to represent a chemical bond; $R^3$ is a substituted or unsubstituted 2-methyl-1-propenyl group or a substituted or unsubstituted isobutyl group; A is oxygen or $NR^8$, wherein $R^8$ represents hydrogen, a substituted or unsubstituted lower alkyl group or a substituted or unsubstituted aryl group; and $R^4$ is hydrogen, a substituted or unsubstituted hydrocarbon group or a substituted or unsubstituted acyl group; and a salt thereof.

In the above formula (I), halogen represented by $R^2$ includes fluorine, chlorine, bromine and iodine.

When $R^1$ and $R^2$ are combined to represent a chemical bond, an epoxy ring is formed.

The hydrocarbon group of the substituted or unsubstituted hydrocarbon group represented by $R^5$, $R^6$ or $R^7$ includes a $C_{1-20}$ hydrocarbon group, preferably a $C_{1-13}$ hydrocarbon group, more preferably a $C_{1-6}$ hydrocarbon group. Examples of the hydrocarbon group include straight- or branched $C_{1-6}$ alkyl (e.g., methyl, ethyl, propyl, isopropyl, butyl, isobutyl, sec-butyl, pentyl, isopentyl, hexyl, etc.), $C_{2-6}$ alkenyl (e.g., vinyl, allyl, 2-butenyl, methylallyl, 3-butenyl, 2-pentenyl, 4-pentenyl, 5-hexenyl, etc.), $C_{2-6}$ alkynyl (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl (e.g., cyclopropyl, cyclobutyl, cyclopentyl, cyclohexyl, etc.), $C_{3-6}$ cycloalkenyl (e.g., cyclobutenyl, cyclopentenyl, cyclohexenyl, cyclohexadienyl, etc.), $C_{7-13}$ aralkyl(e.g., benzyl, 1-phenethyl, 2-phenethyl, etc.), and $C_{6-10}$ aryl(e.g., phenyl, naphthyl, etc.) and the like.

The heterocyclic group of the substituted or unsubstituted heterocyclic group represented by $R^5$, $R^6$ or $R^7$ includes 5- or 6-membered heterocyclic groups containing 1 to 4 heteroatoms (e.g., nitrogen, oxygen, sulfur, etc.), for example, (2-furyl, 2-thienyl, 4-thiazolyl, 4-imidazolyl, 4-pyridyl, 1,3,4-thiadiazol-2-yl, 5-tetrazolyl, etc.) and the like. Further, the heterocyclic group may be condensed with a 5- or 6-membered ring which may contain 1 to 3 heteroatoms (e.g., nitrogen, oxygen, sulfur, etc.) other than carbon atoms (e.g., benzene, pyridine, cyclohexane, etc.) to form a condensed bicyclic group (e.g., 8-quinolyl, 8-purinyl, etc.).

The nitrogen-containing heterocyclic group which may be formed by $R^5$ and $R^6$ together with the adjacent nitrogen atom includes 4- to 7-membered nitrogen-containing heterocyclic group which may contain 1 to 3 heteroatoms (e.g., nitrogen, oxygen, sulfur, etc.) other than the nitrogen atom (e.g., pyrrolidin-1-yl, piperidino, morpholino, piperazin-1-yl, etc.) and the like.

The sulfur-containing heterocyclic group which may be formed by $R^5$ and $R^6$ together with the adjacent sulfur atom includes 4- to 7-membered sulfur-containing heterocyclic groups which may contain 1 to 3 heteroatoms (e.g., nitrogen, oxygen, sulfur, etc.) other than the sulfur atom (e.g., tetrahydrothiophen-1-yl, 1,4-thioxan-1-yl, etc.) and the like.

The nitrogen- or sulfur-containing heterocyclic group which may be formed by $R^5$ and $R^6$ together with the adjacent nitrogen or sulfur atom may be condensed with a 5- or 6-membered ring (e.g., benzene, pyridine, pyrazine, pyrimidine, pyridazine, cyclohexane, etc.) to form a condensed bicyclic group (e.g., isoindolin-2-yl, 2-isoquinolyl, 1,3-dihydrobenzo[c]thiophen-2-yl, 2,3-dihydrobenzo[b]thiophen-1-yl, 1,2,4,5-tetrahydrobenzo[d]thiepin-3-yl, 1,3-dihydrothieno[3,4-c]pyridin-2-yl, 5,7-dihydrothieno[3,4-b]pyrazin-6-yl, 5,7-dihydrothieno[3,4-d]pyridazin-6-yl, etc.) and the like.

The lower alkyl group of the substituted or unsubstituted lower alkyl group represented by $R^8$ includes straight-chain or branched $C_{1-6}$ alkyl groups (e.g., methyl, ethyl, propyl, isopropyl, butyl, isobutyl, sec-butyl, pentyl, isopentyl, hexyl, etc.) and the like.

The aryl group of the substituted or unsubstituted aryl group represented by $R^8$ includes $C_{6-10}$ aryl group (e.g., phenyl, naphthyl, etc.) and the like.

The hydrocarbon group of the substituted or unsubstituted hydrocarbon group represented by $R^4$ includes that described above with respect to that of the substituted or unsubstituted hydrocarbon represented by $R^5$, $R^6$ or $R^7$.

When the hydrocarbon group represented by $R^4$ is an alkenyl group, it preferably has no substituent.

The substituted or unsubstituted acyl group represented by $R^4$ includes residues of substituted or unsubstituted acids, for example, acyl groups derived from the corresponding acids, such as carboxylic acid acyl, sulfonic acid acyl, carbamoyl, thiocarbamoyl and sulfamoyl. Examples of the substituted or unsubstituted acyl include alkanoyl, aroyl, heterocyclic carbonyl, carbamoyl, thiocarbamoyl, arylsulfonyl, alkylsulfonyl, sulfamoyl, alkoxycarbonyl, aryloxycarbonyl and the like. Among them, the carbamoyl group which may have a substituent is the most generally employed.

The alkanoyl group of the above substituted or unsubstituted alkanoyl group includes $C_{1-6}$ alkanoyl groups (e.g., formyl, acetyl, propionyl, isopropionyl, butyryl, pentanoyl, hexanoyl, etc.) and the like.

The aroyl group of the substituted or unsubstituted aroyl group includes $C_{7-11}$ aroyl groups (e.g., benzoyl, 1-naphthoyl, 2-naphthoyl, etc.) and the like.

The heterocyclic carbonyl group of the substituted or unsubstituted heterocyclic carbonyl group includes 5- or 6-membered heterocyclic carbonyl groups containing 1 to 4 heteroatoms (e.g., nitrogen, oxygen, sulfur, etc.), for example, 2-furoyl, 2-thenoyl, nicotinyl, isonicotinyl and the like.

The arylsulfonyl group of the substituted or unsubstituted arylsulfonyl group includes $C_{6-10}$ arylsulfonyl groups (e.g., benzenesulfonyl, 1-naphthylsulfonyl, 2-naphthylsulfonyl, etc.) and the like.

The alkylsulfonyl group of the substituted or unsubstituted alkylsulfonyl group includes $C_{1-6}$ alkylsulfonyl groups (e.g., methylsulfonyl, ethylsulfonyl, etc.) and the like.

The alkoxycarbonyl group of the substituted or unsubstituted alkoxycarbonyl group includes $C_{2-7}$ alkoxycarbonyl groups (e.g., methoxycarbonyl, ethoxycarbonyl, isobutoxycarbonyl, etc.) and the like.

The aryloxycarbonyl group of the substituted or unsubstituted aryloxycarbonyl group includes $C_{7-11}$ aryloxycarbonyl groups (e.g., phenoxycarbonyl, 1-naphthyloxycarbonyl, 2-naphthyloxycarbonyl, etc.) and the like.

Examples of the substituents of the substituted 2-methyl-1-propenyl group or the substituted isobutyl group represented by $R^3$ include hydroxyl, amino, lower ($C_{1-3}$) alkylamino (e.g., methylamino, ethylamino, isopropylamino, etc.), di-lower ($C_{1-3}$) alkylamino (e.g., dimethylamino, diethylamino) and the like. Hydroxyl and di-lower ($C_{1-3}$) alkylamino, particularly dimethylamino, are preferred.

The substituted hydrocarbon group or substituted heterocyclic group represented by $R^5$, $R^6$ or $R^7$; the substituted nitrogen- or sulfur-containing heterocyclic group formed by $R^5$ and $R^6$ together with the adjacent nitrogen or sulfur atom which may be condensed with a further ring; the substituted lower alkyl group or substituted aryl group represented by $R^8$; as well as the substituted hydrocarbon group and substituted acyl group (e.g., alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, etc.) represented by $R^4$ may contain 1 to 3 substituents at any possible positions thereof.

Examples of such substituents include $C_{1-6}$ alkyl groups (e.g., methyl, ethyl, propyl, isopropyl, butyl, isobutyl, sec-butyl, pentyl, isopentyl, hexyl, etc.), $C_{2-6}$ alkenyl groups (e.g., vinyl, allyl, 2-butenyl, methylallyl, 3-butenyl, 2-pentenyl, 4-pentenyl, 5-hexenyl, etc.), $C_{2-6}$ alkynyl groups (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl, etc.), $C_{3-6}$ cycloalkyl groups (e.g., cyclopropyl, cyclobutyl, cyclopentyl, cyclohexyl, etc.), $C_{3-6}$ cycloalkenyl groups (e.g., cyclobutenyl, cyclopentenyl, cyclohexenyl, cyclohexadienyl, etc.), $C_{6-10}$ aryl groups (e.g., phenyl, naphthyl, etc.), amino, mono-$C_{1-6}$ alkylamino groups (e.g., methylamino, ethylamino, isopropylamino, etc.), di-$C_{1-6}$ alkylamino groups (e.g., dimethylamino, diethylamino, etc.), azido, nitro, halogen (e.g., fluorine, chlorine, bromine, iodine, etc.), hydroxyl, $C_{1-4}$ alkoxy groups (e.g., methoxy, ethoxy, etc.), $C_{6-10}$ aryloxy groups (e.g., phenoxy, naphthyloxy, etc.), $C_{1-6}$ alkylthio groups (e.g., methylthio, ethylthio, propylthio, etc.), $C_{6-10}$ arylthio groups (e.g., phenylthio, naphthylthio, etc.), cyano, carbamoyl, carboxyl, $C_{1-4}$ alkoxycarbonyl groups (e.g., methoxycarbonyl, ethoxycarbonyl, etc.), $C_{7-11}$ aryloxycarbonyl groups (e.g., phenoxycarbonyl, 1-naphthyloxycarbonyl, 2-naphthyloxycarbonyl, etc.), carboxy-$C_{1-4}$ alkoxy groups (e.g., carboxymethoxy, 2-carboxyethoxy, etc.), $C_{1-6}$ alkanoyl groups (e.g., formyl, acetyl, propionyl, isopropionyl, butyryl, pentanoyl, hexanoyl, etc.), $C_{7-11}$ aroyl groups (e.g., benzoyl, 1-naphthoyl, 2-naphthoyl, etc.), $C_{1-6}$ alkylsulfonyl groups (e.g., methylsulfonyl, ethylsulfonyl, etc.), $C_{6-10}$ arylsulfonyl groups (e.g., benzenesulfonyl, 1-naphthylsulfonyl, 2-naphthylsulfonyl, etc.), $C_{1-6}$ alkylsulfinyl groups (e.g., methylsulfinyl, ethylsulfinyl, etc.), $C_{6-10}$ arylsulfinyl groups (e.g., benzenesulfinyl, 1-naphthylsulfinyl, 2-naphthylsulfinyl, etc.), 5- or 6-membered heterocyclic groups containing 1 to 4 heteroatoms (e.g., nitrogen, oxygen, sulfur, etc.) (e.g., 2-furyl, 2-thienyl, 4-thiazolyl, 4-imidazolyl, 4-pyridyl, 1,3,4-thiadiazol-2-yl, 5-tetrazolyl, etc.), 5-or 6-membered heterocyclic carbonyl groups containing 1 to 4 heteroatoms (e.g., nitrogen, oxygen, sulfur, etc.) (e.g., 2-furoyl, 2-thenoyl, nicotinoyl, isonicotinoyl, etc.), 5- or 6-membered heterocyclic thio groups containing 1 to 4 heteroatoms (e.g., nitrogen, oxygen, sulfur, etc.) (e.g., 4-pyridiylthio, 2-pyrimidylthio, 1,3,4-thiadiazol-2-ylthio, 5-tetrazolylthio, etc.) and the like. Further, the heterocyclic thio group may be condensed with a benzene ring to form a condensed bicyclic thio group (e.g., 2-benzothiazolylthio, 8-quinolylthio, etc.). Furthermore, when $R^4$ represents a disubstituted carbamoyl, thiocarbamoyl or sulfamoyl group, the substituents together with the nitrogen atom of the carbamoyl, thiocarbamoyl or sulfamoyl group may form a nitrogen-containing heterocyclic group [e.g., 4-to 7-membered nitrogen-containing heterocyclic groups which may contain 1 to 3 heteroatoms (e.g., nitrogen, oxygen, sulfur, etc.) other than the nitrogen atom, such as pyrrolidin-1-yl, piperidino, morpholino, piperazin-1-yl, 4-methylpiperazin-1-yl, 4-phenylpiperazin-1-yl, etc.].

The substituent in the substituted hydrocarbon group or substituted heterocyclic group represented by $R^5$, $R^6$ or $R^7$; the substituent in the substituted nitrogen- or sulfur-containing heterocyclic group which may be formed by $R^5$ and $R^6$ together with the adjacent nitrogen or sulfur atom and may be condensed with a further ring; the substituent in the substituted lower alkyl group or substituted aryl group represented by $R^8$; as well as the substituent in the substituted hydrocarbon group or substituted acyl group (e.g., alkanoyl, aroyl, heterocyclic carbonyl, carbamoyl, thiocarbamoyl, arylsulfonyl, alkylsulfonyl, sulfamoyl, alkoxycarbonyl, aryloxycarbonyl, etc.) represented by $R^4$ may further contain 1 to 3 substituents at the possible positions.

Examples of such substituents include the aforementioned $C_{1-6}$ alkyl groups, $C_{2-6}$ alkenyl groups, $C_{2-6}$ alkynyl groups, $C_{3-6}$ cycloalkyl groups, $C_{3-6}$ cycloalkenyl groups, $C_{6-10}$ aryl groups, amino, mono-$C_{1-6}$ alkylamino groups, di-$C_{1-6}$ alkylamino groups, azido, nitro, halogen, hydroxyl, $C_{1-4}$ alkoxy groups, $C_{6-10}$ aryloxy groups, $C_{1-6}$ alkylthio groups, $C_{6-10}$ arylthio groups, cyano, carbamoyl, carboxyl, $C_{1-4}$ alkoxycarbonyl groups, $C_{7-11}$ aryloxycarbonyl groups, carboxy-$C_{1-4}$ alkoxy groups, $C_{1-6}$ alkanoyl groups, halogeno $C_{1-6}$ alkanoyl groups, $C_{7-11}$ aroyl groups, $C_{1-6}$ alkylsulfonyl groups, $C_{6-10}$ arylsulfonyl groups, $C_{1-6}$ alkylsulfinyl, $C_{6-10}$ arylsulfinyl groups, 5- or 6-membered heterocyclic groups, 5- or 6-membered heterocyclic carbonyl groups, 5- or 6-membered heterocyclic thio groups and the like.

The counter anion represented by $X^-$ includes, for example, halogenide ions (e.g., iodide ion, bromide ion, chloride ion, etc.), sulfate ion, phosphate ion, nitrate ion, perchlorate ion, tetrafluoroborate ion, methanesulfate ion, p-tolylsulfate ion, benzenesulfate ion, hydroxyl ion, organic carboxylate ions (e.g., oxalate ion, maleate ion, fumarate ion, succinate ion, citrate ion, lactate ion, trifluoroacetate ion, lactobionate ion, acetate ion, propionate ion, tartrate ion, ethyl succinate ion, etc.) and the like.

The compound (I) has asymmetric centers in its molecule and is optically active. The mode of bonding of the substituents on the cyclohexane ring is represented where ------ is an α-bond, ━━ is a β-bond and, ────── is either α-bond or β-bond.

The absolute configuration other than the mode of bonding of the substituents on the cyclohexane ring is the same as that of the starting fumagillol.

In the compound (I), preferably, $R^1$ and $R^2$ are combined to represent a chemical bond, or $R^1$ is hydrogen and $R^2$ is $N(O)_mR^5R^6$, $N^+R^5R^6R^7 \cdot X^-$, $S(O)_nR^5$ or $S^{+R5}R^6 \cdot X^-$. More preferably, $R^2$ is $S^+R^5R^6 \cdot X^{31}$ in which $R^5$ and $R^6$ are independently a hydrocarbon group and $X^-$ is a halogenide ion. The compounds of the formula (I) wherein $R^1$ and $R^2$ are combined to represent a chemical bond are particularly preferred.

────── A is preferably ──────── A

A is preferably oxygen or NH, more preferably oxygen.

$R^3$ is preferably a 2-methyl-1-propenyl or isobutyl group which is unsubstituted or substituted with (1) hydroxyl or (2) dialkylamino group, and more preferably 2-methyl-1-propenyl.

$R^4$ is preferably a substituted carbamoyl group or a substituted ureido group, and particularly preferably a substituted carbamoyl group. The said substituents are preferably $C_{1-6}$ alkanoyl which may be substituted with (1) a $C_{1-6}$ alkyl group or (2) a halogen. When the compound (1) has the following substituents, it is generally employed.

(1) $R^1$ and $R^2$ are combined to form an epoxy ring.

(2) A is oxygen.

(3) $R^3$ is a 2-methyl-1-propenyl group or isobutyl group which may be substituted with hydroxyl group or di-lower alkylamino group.

(4) $R^4$ is a substituted or unsubstituted acyl group, more preferably, a carbamoyl group substituted with one to three of $C_{1-6}$ alkanoyl groups which may be substituted with one to three of halogens.

(5) $R^1$ and $R^2$ are combined to form an epoxy ring, A is oxygen, $R^3$ is 2-methyl-1-propenyl group and $R^4$ is a carbamoyl substituted with monochloroacetyl or dichloroacetyl.

(6) $R^1$ and $R^2$ are combined to form an epoxy ring, A is oxygen, $R^3$ is isobutyl group and $R^4$ is a carbamoyl substituted with monochloroacetyl or dichloroacetyl.

(7) $R^1$ and $R^2$ are combined to form an epoxy ring, A is oxygen, $R^3$ is 2-methyl-1-propenyl group and $R^4$ is a carbamoyl substituted with monochloroacetyl.

Preferred examples of the compound (I) include 6-0-(N-chloroacetylcarbamoyl) fumagillol, 6α-(N'-chloroacetyl-ureido)-6-deoxyfumagillol, 4-(N'-chloroacetylureido)-2-(1, 2-epoxy-1,5-dimethyl-4-hexenyl)-1-(1,3-dihydrobenzo[c]thiophen-2-ylio)-3-methoxycyclohexanol chloride, 6-0-(N-methylcarbamoyl)fumagillol and the like. In particular, 6-0-(N-chloroacetylcarbamoyl) fumagillol and 6-0-(N-methylcarbamoyl)fumagillol are preferred.

When the compound (I) has an acidic substituent (e.g., carboxyl, etc.) or a basic substituent (e.g., amino, mono-lower alkylamino, di-lower alkylamino, nitrogen-containing heterocyclic group, etc.) in the molecule, the compound (I) may form a physiologically acceptable salt thereof. Examples of the physiologically acceptable salt include those with inorganic bases, organic bases, inorganic acids, organic acids, basic or acidic amino acids and the like. As the inorganic base which can form these salts, there are, for example, alkali metals (e.g., sodium, potassium, etc.) and alkaline earth metals (e.g., calcium, magnesium, etc.) and the like; as the organic base, there are, for example, trimethylamine, triethylamine, pyridine, picoline, N,N-dibenzylethylenediamine, ethanolamine, diethanolamine, tris(hydroxymethyl) aminomethane, dicyclohexylamine and the like; as the inorganic acid, there are, for example, hydrochloric acid, hydrobromic acid, sulfuric acid, nitric acid, phosphoric acid and the like; as the organic acid, there are, for example, formic acid, acetic acid, trifluoroacetic acid, oxalic acid, tartaric acid, fumaric acid, maleic acid, methanesulfonic acid, benzensulfonic acid, p-toluenesulfonic acid and the like; and as the basic or acidic amino acid, there are, for example, arginine, lysine, ornithine, aspartic acid, glutamic acid and the like.

The above salts with bases (i.e., salts with inorganic bases, salts with organic bases, salts with basic amino acids) are formed by the bases and the carboxyl group in the substituent of the compound (I). The above salts with acids (i.e., salts with inorganic acids, salts with organic acids, salts with acidic amino acids) are formed by the acids and amino, mono-lower alkylamino groups, di-lower alkylamino groups, nitrogen-containing heterocyclic groups and the like in the substituent of the compound (I).

When the compound (I) has a di-lower alkyl amino group, a nitrogen-containing heterocyclic group or a nitrogen-containing aromatic heterocyclic group, the nitrogen atom in these groups may be further alkylated to form a quaternary ammonio group (e.g., trimethylammonio, N-methylpyridinyl, N-methylpyrrolidin-1-ylium, etc.), and the counter anion thereof includes the counter anions shown with respect to those represented by $X^-$.

The compound represented by the formula (I) or a salt thereof can be produced by using, as a starting material, fumagillol [Tarbell, D. S. et al., J. Am. Chem. Soc., 83, 3096 (1961)] which is a hydrolyzate of fumagillin produced by a microorganism, by per se known processes, for example, acylation, carbamoylation, alkylation, sulfonilation and so on. The processes described in, for example, JP Kokai 279828/89 (EP-A-325,199), JP Kokai 7270/91(EP-A-359,036), JP Kokai 7222/91(EP-A-357,061), JP Kokai 14571/91(EP-A-386,667), JP Kokai 7271/91(EP-A-387,650), JP Kokai 279376/91(EP-A-415,294), JP Kokai 76866/90 (EP-A-354,767), EP-A-354,787 and the like or modifications thereof.

The fumagillol derivatives represented by the general formula (I) may be formulated as salts thereof or complexes prepared by known pharmaceutical preparation methods. For example, in order to increase their water-solubility, promote their absorption and increase their pharmacological activities, the fumagillol derivatives may be used as complexes with cyclodextrin compounds.

The above complexes of fumagillol derivatives or salts thereof and cyclodextrin compounds can be prepared, for example, by the method described in JP Kokai 297469/92 (e.g., the method wherein a fumagillol derivative or a salt thereof and a cyclodextrin compound are dissolved in water, and the solution is stirred at room temperature (−10° C. to 35° C.) to 80° C. or modifications thereof.

The corneal opacification inhibitory composition of this invention can be used as an ophthalmic preparation. Examples of the ophthalmic preparation include ophthalmic solution, ophthalmic suspension, ophthalmic ointment and the like.

The corneal opacification inhibitory composition of this invention, as is clear from the test examples mentioned below, has an excellent inhibitory effect against corneal opacification, and therefore, can be employed as a potent pharmaceutical for prophylaxis and treatment of corneal opacification. The corneal opacification includes, for example, that occurring after various kinds of ophthalmic surgery which are exemplified by laser ablation, particularly, photorefractive keratectomy treatment for myopia, hyperopia, astigmatism, etc. with excimer laser and the surgery for cataract and glaucoma and the like.

The present corneal opacification inhibitory composition has low toxicity, and can be administered safely to mammals (e.g., humans, monkeys, dogs, cats, rabbits, mice etc.)

The corneal opacification inhibitory composition of this invention can generally be formulated as pharmaceutical preparation according to per se known methods by for example, admixing, suspending or dissolving the fumagillol derivatives of the general formula (I) and a salt thereof with per se known ophthalmologically acceptable carriers, excipients or the like.

The ophthalmologically acceptable carrier or excipient includes, for example, a solvent, suspending or dispersing medium, ointment base and the like which are usually employed in the ophthalmic preparation.

When the corneal opacification inhibitory composition of this invention is in a form of an ophthalmic solution, it can be prepared, for example, by adding the aforementioned fumagillol derivative or a salt thereof to a solvent (e.g., sterilized pure water etc.), which is heated if necessary, and dissolving completely in the solvent.

When the corneal opacification inhibitory composition of this invention is in the form of ophthalmic suspension, it can be formulated by, for example, suspending the aforementioned fumagillol derivative or a salt thereof in a suspending media (e.g., sterilized pure water etc.) which is heated if necessary.

Further, an ophthalmic solution or ophthalmic suspension may be prepared by lyophilizing the aforementioned fumagillol derivative or a salt thereof according to per se known methods and by dissolving or suspending it in an eluent at the time it is used.

When the corneal opacification inhibitory composition is in the form of ophthalmic ointment, it can be prepared by admixing the aforementioned fumagillol derivative or a salt thereof with, for example, an opthalmic ointment base (e.g., hydrocabon gel, lanolin, petrolatum, liquid paraffin etc.) which may be heated if necessary.

Examples of the solvents include, for example, sterilized pure water, injectable distilled water, vegetable oils such as castor oil and the like. Among them, sterilized pure water is preferable.

The ophthalmic ointment bases are exemplified by prepared lanolin, petrolatum, hydrocarbon gel, liquid paraffin and the like. Among them, hydrocabon gel is preferable.

There may optionally be used additives such as preservatives, solution adjuvants, suspending agents, buffering agents, isotonicity agents, pH adjustors, thickening agents, chelating agents and the like which can usually be employed for ophthalmic preparations unless it is unsuited for the purpose of the present invention.

Examples of preservatives include, benzalkonium chloride, benzetonium chloride, such parahydroxy benzoates as methyl parahydoxybenzoate, ethyl parahydroxybenzoate, propyl parahydroxybenzoate, butyl parahydroxybenzoate, benzyl alcohol, phenetyl alcohol, sorbic acid or a salt thereof, thimerosal, chlorobutanol and the like. The concentration of the preservatives in a ophthalmic preparation is preferably about 0.001 to 0.5 w/v % and more preferably about 0.003 to 0.1 w/v %.

The solution adjuvants are exemplified by cyclodextrin derivatives, polyvinylpyrrolidone, polyvinylalcohol, polyethyleneglycol and the like.

Examples of suspending agents include polysorbate 80 and the like.

As the buffering agents, there may be mentioned, for example, phosphate buffers, carbonate buffers, borate buffers, citrate buffers, tartrate buffers, acetate buffers, amino acids and the like.

Examples of isotonicity agents include saccharides such as sorbitol, glucose, mannitol, polyhydric alcohols such as glycerin, polyethylene glycol, propylene glycol, salt such as sodium chloride and the like.

As for pH adjustors, there may be mentioned, for example, hydrochloric acid, acetic acid, phosphoric acid, sodium hydroxide, borax and the like.

Examples of thickening agents include hydroxyethyl cellulose, hydroxypropyl cellulose, methyl cellulose, hydroxypropylmethyl cellulose, carboxymethyl cellulose, salts thereof and the like.

Chelating agents include, for example, sodium edetate, sodium citrate, condensed sodium phosphate and the like.

The present corneal opacification inhibitory composition may optionally contain one or more of other corneal opacification inhibitory agents unless it is unsuited for the purpose of the present invention.

Other pharmaceutically active components may optionally be added to the present corneal opacification inhibitory composition unless it is unsuited for the purpose of this invention. Examples of the other pharmaceutically effective components include antibiotics (e.g. erythromycin, cefmenoxime, chloramphenicol, sulbenicillin, tobramycin, gentamicin, sisomicin, dibekacin, micronomicin, colistin, tetramycin, etc.), synthetic antibacterial agents (e.g. lomefloxacin, ofloxacin, norfloxacin, etc.), steroidal antiinflammatory agents (e.g. predonisolone, methyl predonisolone, betamethasone phosphate, dexamethasone, fluorometholone, etc.), non-steroidal antiinflammatory agents (e.g. indomethacin, pranoprofen, diclofenac, azulene, etc.).

The dose of the corneal opacification inhibitory composition of this invention varies with preparetion for administration, symptom, age and body weight of the patient, etc. For example, when administered to human adults, it is preferably administered as an ophthalmic preparation which contains about 0.001 to 10 w/v %, preferably about 0.003 to 2 w/v %, more preferably, about 0.01 to 0.2 w/v % of the fumagillol derivatives as the effective component. The dosage can readily be determined for different ages, body weights, and according to the symptoms of the patients by those skilled in the art based upon the present disclosure.

When the preparation is in the form of an ophthalmic solution or suspension, the preparations which contain the effective component in the aforesaid concentration are preferably administered in a dose of 50 to 200 μl, 1 to 5 times a day and when the preparation is in a form of ophthalmic ointment, preferably administered 1 to 5 times a day.

A preferred method of administration of the ointment is to put the ointment sideways thinly on the conjunctival sac with an ophthalmic swab and to massage the eyelid softly.

The following working examples and test examples illustrate the present invention concretely, but are not to be construed to limit the scope of the invention.

EXAMPLE 1

Ophthalmic solution

| Formulation | |
|---|---|
| 6-0-(N-chloroacetylcarbamoyl)fumagillol (hereinafter referred to as Compound A) | 0.05 g |
| sodium acetate | 0.1 g |
| mannitol | 5.0 g |
| methyl parahydroxybenzoate | 0.026 g |
| propyl parahydroxybenzoate | 0.014 g |
| acetic acid | q.s. |
| sterilized pure water | ad. 100 ml (pH 5.0) |

Preparation method 95 ml of sterilized pure water was heated and methyl parahydroxybenzoate, propyl hydroxybenzoate, sodium acetate and mannitol were dissolved in the water.

Compound A was dissolved thereto and the solution was adjusted to pH 5.0 with acetic acid. Sterilized pure water was added to make a total amount 100 ml. The solution was filtered with a 0.22 μm membrane filter. An ophthalmic container was filled with the solution thus obtained.

EXAMPLE 2

Ophthalmic solution

| Formulation | |
|---|---|
| Compound A | 0.05 g |
| boric acid | 1.7 g |
| methyl parahydroxybenzoate | 0.026 g |
| propyl parahydroxybenzoate | 0.014 g |
| sodium acetate | 0.005 g |
| borax | q.s. |
| sterilized pure water | ad. 100 ml (pH 5.5) |

Preparation method

In 95 ml of hot sterilized pure water methyl parahydroxybenzoate, propyl parahydroxybenzoate, boric acid and sodium edetate were added and then Compound A was dissolved. The solution was adjusted to pH 5.5 with borax. Sterilized pure water was added to make a total amount 100 ml and the solution was filtered with a 0.45 μm membrane filter. A container was filled with the solution thus obtained.

EXAMPLE 3

Ophthalmic suspension

| Formulation | |
|---|---|
| Compound A | 0.5 g |
| disodium hydrogenphosphate dihydrate | 0.1 g |
| sodium chloride | 2.5 g |
| polysorbate 80 | 0.1 g |
| benzalkonium chloride | 0.005 g |
| acetic acid | q.s. |
| sterilized pure water | ad. 100 ml (pH 7.5) |

Preparation method

95ml of sterilized pure water was heated followed by dissolving disodium hydrogenphosphate dihydrate, sodium chloride, benzalkonium chloride and polysorbate 80.

Compound A was suspended in the solution and the suspension was adjusted to pH 7.5 with acetic acid. Another sterilized pure water was added to make a total amount 100 ml and the suspension was filled into a container to obtain an ophthalmic suspension.

EXAMPLE 4

Ophthalmic preparation

| Formulation of lyophilized product for one vial bottle | |
|---|---|
| Compound A | 0.0025 g |
| mannitol | 0.25 g |
| sterilized pure water | ad. 30 ml |
| Formulation of 5 ml eluent | |
| trisodium citrate | 0.005 g |
| acetic acid | q.s. |
| methyl parahydroxybenzoate | 0.0001 g |
| propyl parahydroxybenzoate | 0.0005 g |
| sterilized pure water | ad. 5 ml |
| | (pH 5.0) |

Preparation method

1) Compound A and mannitol were dissolved in a sterilized pure water and another sterilized pure water was added to make a total amount 30 ml. The solution was lyophilized to obtain a lyophilized product.

2) In 4 ml sterilized pure water methyl parahydroxybenzoate, propyl parahydroxybenzoate, trisodium citrate were dissolved followed by adjusting to pH 5.0 with acetic acid. Sterilized pure water was added to make a total amount 5 ml. After sterilizing the solution by filtration with a 0.22 μm membrane filter, the solution was filled into a container to obtain an eluent.

3) The above-mentioned lyophilized product is to be dissolved with 5 ml of the dissolving solution to make an ophthalmic solution at the time when used.

EXAMPLE 5

Ophthalmic ointment

| Formulation | |
|---|---|
| Compound A | 0.05 g |
| glycerin | 2.0 g |
| propyleneglycol | 1.0 g |
| liquid paraffin | 2.0 g |
| methyl parahydroxybenzoate | 0.03 g |
| propyl parahydroxybenzoate | 0.01 g |
| white petrolatum | ad. 100 g |

Preparation method

To the mixture of glycerin and propyleneglycol were added liquid paraffin, methyl parahydroxybenzoate, propyl parahydroxybenzoate and Compound A. White petrolatum was added to make a total amount 100 g followed by mixing the mixture. The mixture was filled into a container to obtain an ophthalmic ointment.

EXAMPLE 6

Ophthalmic ointment

| Formulation | |
|---|---|
| Compound A | 0.05 g |
| glycerin | 2.0 g |
| propyleneglycol | 1.0 g |

-continued

| Formulation | |
|---|---|
| liquid paraffin | 2.0 g |
| ethyl parahydroxybenzoate | 0.01 g |
| propyl parahydroxybenzoate | 0.01 g |
| hydrocabon gel | ad. 100 g |

Preparation method

To the mixture of glycerin and propyleneglycol were added liquid paraffin, ethyl parahydroxybenzoate, propyl parahydroxybenzoate and Compound A. Plastibase was added to make a total amount 100 g followed by mixing the mixture. The mixture was filled into a container to obtain an ophthalmic ointment.

EXAMPLE 7

Ophthalmic solution

| Formulation | |
|---|---|
| Compound A | 0.05 g |
| concentrated glycerin | 2.6 g |
| disodium hydrogenphosphate dihydrate | 0.1 g |
| methyl parahydroxybenzoate | 0.026 g |
| propyl parahydroxybenzoate | 0.014 g |
| sodium hydroxide | q.s. |
| sterilized pure water | ad. 100 ml |
| | (pH 6.0) |

Preparation method

In 95 ml of hot sterilized pure water were dissolved methyl parahydroxybenzoate, propyl parahydroxybenzoate, concentrated glycerin and disodium hydrogenphosphate dihydrate.

Compound A was dissolved thereto and the solution was adjusted to pH 6.0 with sodium hydroxide. Another sterilized pure water was added to make a total amount 100 ml. After sterilizing the solution was filled into a container to obtain an ophthalmic solution.

EXAMPLE 8

Ophthalmic solution

| Formulation | |
|---|---|
| Compound A | 0.05 g |
| sodium acetate | 0.1 g |
| mannitol | 5.0 g |
| acetic acid | q.s. |
| sterilized pure water | ad. 100 ml |
| | (pH 5.0) |

Preparation method

In 95 ml of hot sterilized pure water were dissolved sodium acetate, mannitol, and then Compound A. The solution was adjusted to pH 5.0 with acetic acid. Sterilized pure water was added to make a total amount 100 ml. After sterilizing the solution with a 0.22 μm membrane filter, the solution was filled into a container to obtain an ophthalmic solution.

TEST EXAMPLE 1

Test compounds

Compound A was used as the composition prepared in Example 8.

Rinderon(Registered Trademark, 0.1% sodium betamethasone phosphate ophthalmic solution; steroidal antiinflammatory agent produced by Shionogi Pharmaceutical Co., Ltd.) was used as a positive control.

phisiological saline was used as a control.

Test method

Twenty one male Brown Norway series rats, ca. 250 g of body weight, 9–10 weeks old, were anesthetized with ketaral, and Benoxil ophthalmic solution was dropped on the eyes of the rats to put them under local anesthesia.

Determining the conditions for excimer laser ablation as a 2.5 mm ablation in diameter, 50 Hz frequency, 160 mJ/cm$^2$ power, 60 scans, 0.8 μm/scan ablation rate, superficial keratectomy was performed on the both eyes of the rats with excimer laser.

The rats underwent superficial keratectomy were divided into 3 groups of 7 animals each. Five μl each of Compound A solution, Rinderon solution or physiological saline was dropped on the eyes of the each group twice a day immediately after the laser ablation and 4 times a day after the next day, followed by dropping ofloxacin ophthalmic solution (Tarivid: Registered Trademark, produced by Santen Pharmaceutical Co., Ltd.) each time. The rats were fed on Labo MR Stock, produced by Nihon Nosan Kogyo Kabushikikaisha (Japan Agricultural Products Industries, Ltd.) and given water freely in a breeding room air-conditioned at 23°±2° C. and 55±10% humidity.

Results

Six days after the superficial keratectomy, the corneas were observed with a slit lamp and the degree of corneal opacification was evaluated according to the following criteria and % inhibition were calculated. The results were shown in Table 1.

0: no opacification

1: slightly opaque all over (easy to see the iris through the cornea)

2: rather opaque partly (rather difficult to see the iris through the cornea)

3: rather opaque all over

4: heavily opaque partly (difficult to see the iris through the cornea)

5: heavily opaque all over

TABLE 1

Inhibitory effects of corneal opacification

| Group | Evaluation (average value) | Inhibition (%) |
| --- | --- | --- |
| Control | 3.9 | — |
| Positive control | 3.3 | 15.2 |
| Compound A | 2.1* | 45.1 |

*: The group treated with Compound A was significantly differentiated from the control group by the calculation of Dunnett's multicomparison method (5% risk).

As is shown from Table 1, the evaluation value of the group treated with Compound A is 2.1, while that of the control group is 3.9 and that of the positive control group is 3.3, and it is clear that the composition of this invention has an excellent corneal opacification inhibitory effect. It was also confirmed by the calculation of Dunnett's multicomparison method that Compound A inhibited significantly the corneal opacification while the positive control could not do significantly.

Regarding the % inhibition of corneal opacification relative to the control group, that of the Compound A was 45.1% while that of the positive control was 15.2% and Compound A showed an excellent corneal opacification inhibitory effect.

TEST EXAMPLE 2

Test method

The superficial keratectomy was performed on eyes of twelve male Brown Norway rats, ca.250 g body weight/animal, 9 to 10 weeks old, according to the manner similar to that in Test Example 1. The rats underwent superficial keratectomy and were divided into 3 groups of 4 animals each.

According to the manner similar to that of Test Example 1, the rats were treated with Compound A, Rinderon (positive control) or physiological saline (control). Seven days after the superficial keratectomy, the eyeballs of the rats were extracted to prepare pathological tissue specimens according to the usual manner. Hematoxylin and eosine sections were prepared from the formalin fixed specimens. The fibroblastic cell layers invaded into about one third portion (a central part) of the laser ablated area under corneal epithelium were measured under a microscope and histological evaluation was performed.

Numbers of fibroblastic cell layers under corneal epithelium were counted and the % inhibition was calculated as shown in Table 2.

Results

TABLE 2

Numbers of fibroblastic cell layer under corneal epithelium.

| Group | Number of layer (average value) | Inhibition (%) |
| --- | --- | --- |
| Control | 10.5 | — |
| Positive control | 6.5* | 38.1 |
| Compound A | 1.3** # | 87.6 |

By the calculation of Dunnett's multicomparison method;
*: significantly differentiated with 5% risk from the control group.
**: significantly differentiated with 1% risk from the control group.
: significantly differentiated with 1% risk from the positive control group.

As shown in Table 2, the numbers of fibroblastic cell layers under corneal epithelium in the group treated with Compound A was 1.3, while that in the control group was 10.5 and that of the positive control group is 6.5. Therefore, the group treated with Compound A has a significantly fewer layers compared with those of the control and positive control groups, while the % inhibition of fibroblastic cell layers under corneal epithelium in the positive control group was 38.1, that in the group treated with Compound A was 87.6%. That shows clearly that Compound A has a very excellent corneal opacification inhibitory activity.

EFFECTS OF THIS INVENTION

The composition of this invention shows low toxicity and has an excellent inhibitory activity against corneal opacification after ophthalmic surgery. Therefore it is useful for treatment such as prevention and healing of corneal opacification occurring after ophthalmic surgery.

What we claim is:

1. A method of treating corneal opacification which comprises administering a corneal opacification inhibitory amount of a fumagillol derivative of the formula (I):

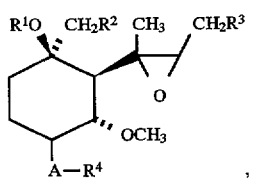
(I)

wherein $R^1$ is hydrogen; $R^2$ is a halogen, $N(O)_m R^5 R^6$, $N^+ R^5 R^6 R^7 \cdot X^-$, $S(O)_n R^5$ or $S^+ R^5 R^6 \cdot X^-$ wherein $R^5$ $R^6$ and $R^7$ represent independently a substituted or unsubstituted hydrocarbon group or a substituted or unsubstituted heterocyclic group; $X^-$ represents a counter anion; m represents 0 or 1; n represents an integer from 0 to 2; or $R^5$ and $R^6$ together with the adjacent nitrogen or sulfur atom may form a substituted or unsubstituted nitrogen- or sulfur-containing heterocyclic group which may form a condensed ring; or $R^1$ and $R^2$ are combined to represent a chemical bond; $R^3$ is a substituted or unsubstituted 2-methyl-1-propenyl group or a substituted or unsubstituted isobutyl group; A is oxygen or $NR^8$, wherein $R^8$ represents hydrogen, a substituted or unsubstituted lower alkyl group or a substituted or unsubstituted aryl group; and $R^4$ is hydrogen, a substituted or unsubstituted hydrocarbon group or a substituted or unsubstituted acyl group or a salt thereof, to a subject undergoing ophthalmic surger.

2. The method according to claim 1, wherein the ophthalmic surgery is laser ablation.

3. The method according to claim 1, wherein the ophthalmic surgery is photorefractive keratectomy with excimer laser.

4. The method according to claim 1, wherein a fumagillol derivative of the formula (I) is 6-0-(N-chloroacetylcarbamoyl) fumagillol or a salt thereof.

* * * * *